United States Patent [19]

Lasley

[11] Patent Number: 4,509,513

[45] Date of Patent: Apr. 9, 1985

[54] PORTABLE AND COLLAPSIBLE HYPERBARIC CHAMBER ASSEMBLY

[76] Inventor: Robert A. Lasley, 508 Sentinel Rd., Moorestown, N.J. 08057

[21] Appl. No.: 426,634

[22] Filed: Sep. 29, 1982

[51] Int. Cl.³ .............................................. A61H 9/00
[52] U.S. Cl. ........................... 128/202.12; 128/205.26
[58] Field of Search .............. 128/205.26, 113, 202.12, 128/24 R, 30, 30.2, 201.29, 361, 31, 368, 402; 604/313, 315, 316

[56] References Cited

U.S. PATENT DOCUMENTS

| 2,832,336 | 4/1958 | Davis et al. ........................ 128/402 |
| 3,062,215 | 11/1962 | Heyns ................................... 128/361 |
| 3,602,221 | 8/1971 | Bleicken ......................... 128/205.26 |
| 3,786,809 | 1/1974 | Kitrilakis ....................... 128/205.26 |
| 4,367,728 | 1/1983 | Mutke ............................ 128/205.26 |
| 4,432,354 | 2/1984 | Lasley ................................... 128/30 |

Primary Examiner—Henry J. Recla
Assistant Examiner—Karin M. Reichle
Attorney, Agent, or Firm—Witherspoon & Hargest

[57] ABSTRACT

A portable and collapsible hyperbaric chamber assembly adapted to accomodate the major portion of a patient's body and adapted for connection to a pressurized source of oxygen or other suitable gas. The chamber assembly includes a circular frame which is U-shaped in cross section wherein the closed end of the U is the frame base and the depending portions form the inner and outer frame walls. A flexible tubular chamber member is secured to the outer frame wall and extends downwardly therefrom while a sealing sleeve is connected to the inner wall of the frame. The frame base has connections for receiving pressurized oxygen or other suitable gas. A patient is positioned within the tubular chamber member with the sealing sleeve sealingly contacting the upper portion of his body after which the tubular chamber member is folded below the patient's feet to form an airtight seal whereby an airtight chamber is provided between the tubular chamber member and the sealing sleeve to receive the pressurized oxygen or other suitable gas as required for treatment.

6 Claims, 4 Drawing Figures

FIG. 4.
FIG. 3.
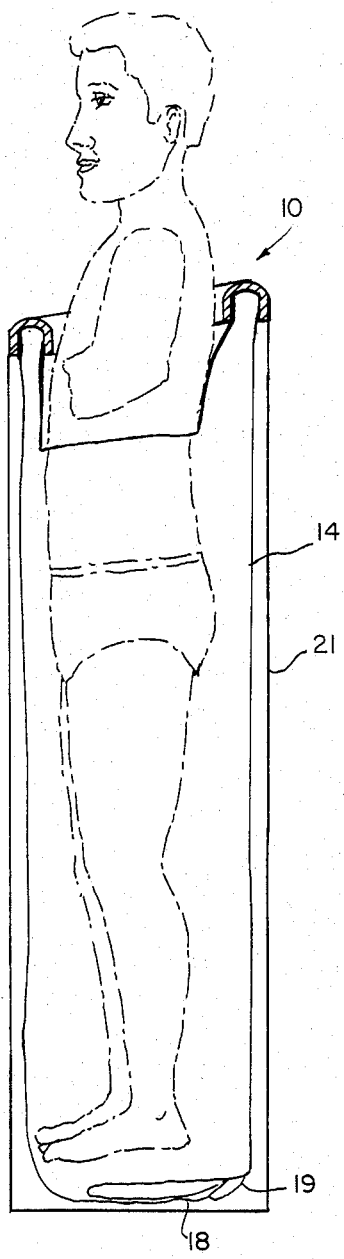
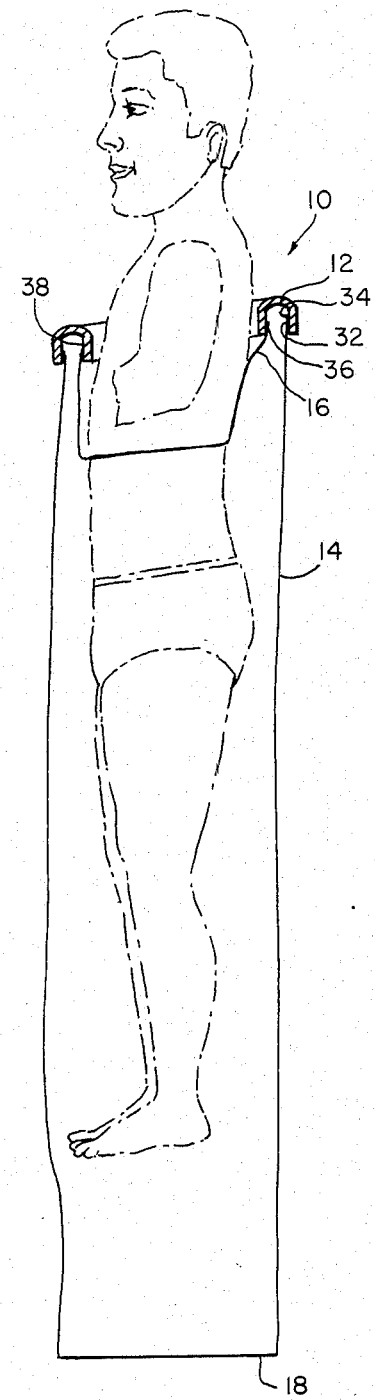

PORTABLE AND COLLAPSIBLE HYPERBARIC CHAMBER ASSEMBLY

BACKGROUND AND SUMMARY OF THE INVENTION

This invention relates to hyperbaric chambers and more particularly to an improved hyperbaric chamber of a universal nature wherein the chamber itself is flexible and adjustable. The therapeutic value of hyberbaric chambers is well known particularly with regard to certain types of wounds. Therefore such will not be further elaborated upon herein.

A large number of hyperbaric chambers are made of rigid heavy materials and thus constitute rather heavy and clumsy units. The need for a more or less universal type of hyperbaric chamber is quite evident yet no one has come up with such a unit. In addition, it would be desirable to have a unit which is inexpensive so that it may become a throw-away item and thus obviate the need for sterilization after use.

In view of the foregoing it is an object of this invention to provide a hyperbaric chamber assembly wherein the chamber itself is collapsible and adjustable.

It is another object of this invention to provide a hyperbaric chamber assembly which is inexpensive so that it may be considered a throw-away item.

It is yet another object of this invention to provide a hyperbaric chamber assembly which is very light in weight so that it may be readily moved from place to place.

It is a still further object of this invention to provide a soft flexible hyperbaric chamber whereby the patient can move about comfortably and is not required to maintain a virtually rigid position for the treatment time.

The above and additional objects and advantages will become more apparent when taken in conjunction with the accompanying detailed description and drawings, describing one preferred embodiment of this invention.

IN THE DRAWINGS

FIG. 1 is a plan view illustrating the frame of the hyperbaric chamber of this invention and the hook up to pressurized oxygen control assembly, FIG. 2 is a cross sectional view of the hyperbaric chamber frame showing the flexible tubular chamber member and the sealing sleeve both rolled up and positioned generally within the chamber frame, FIG. 3 is an elevational view partly in section illustrating the position of a patient within the chamber with the flexible tubular chamber member extending downwardly below his feet and the sealing sleeve engaging his chest region, and FIG. 4 is a view similar to that of FIG. 3 and in addition shows the flexible tubular chamber member folded over so as to form an air-tight seal at the bottom thereof and with a reinforcing sheath extending completely around the bubular chamber member.

DETAILED DESCRIPTION OF THE INVENTION

Figure 1:
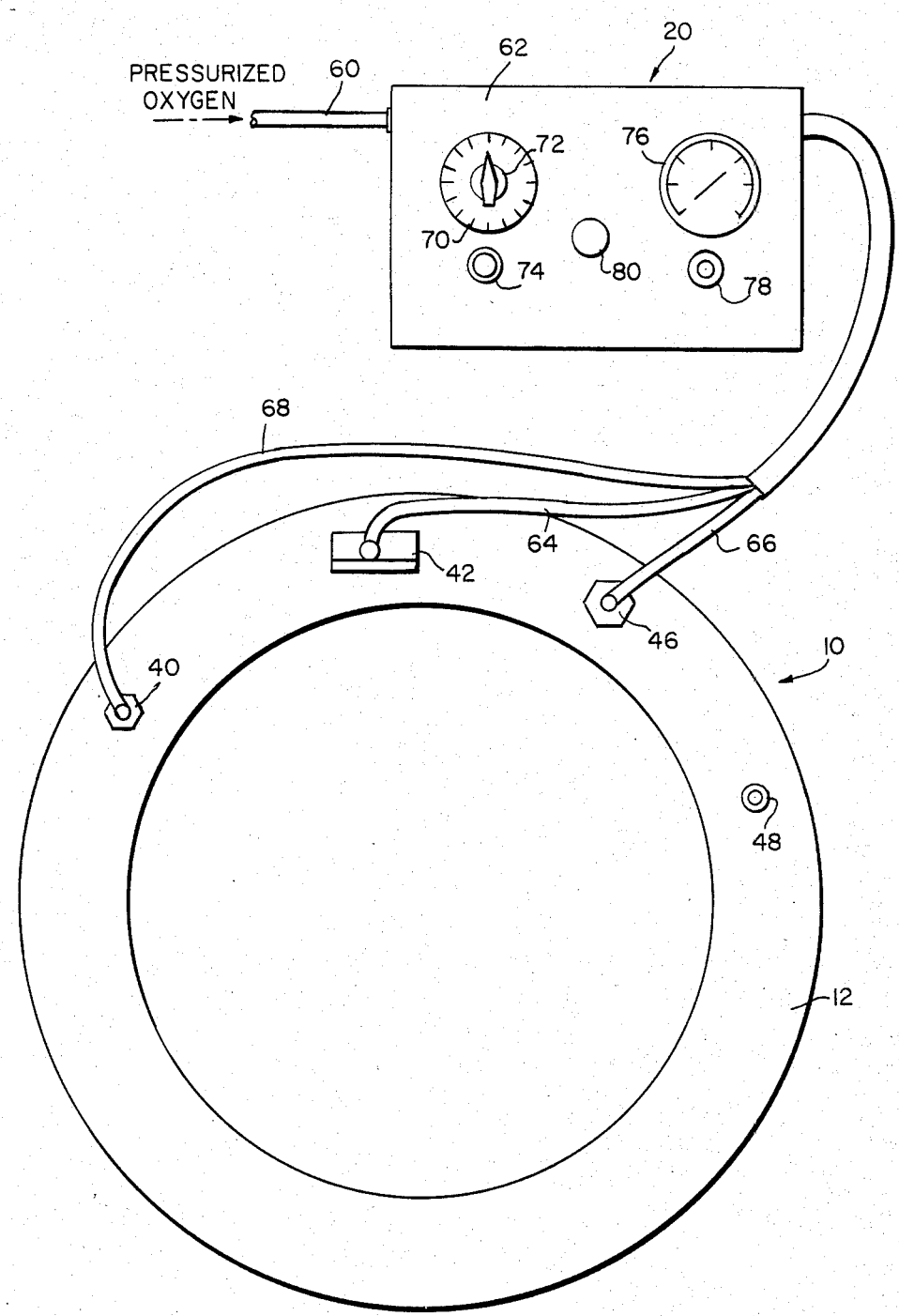

Referring to FIGS. 1-4 of the drawings, the portable and collapsible hyperbaric chamber assembly 10 comprises a circular frame 12 having a flexible tubular chamber member 14 and a thin elastic sealing sleeve 16 extending downwardly therefrom. The bottom of the flexible tubular chamber member 14 may be folded over at its bottom 18 (see FIG. 4) for sealing purposes. The chamber assembly 10 is adapted for connection to a unit 20 which provides the chamber with pressurized oxygen or other suitable gas and also exhausts same.

More particularly, the chamber assembly 10 comprises a circular frame 12 having a U-shaped cross section wherein the closed portion of the U constitutes the frame base 22. An outer wall portion 24 extends downwardly from the outer edge 26 of the frame base 22 while an inner wall portion 28 extends downwardly from the inner edge 30 of the frame base 22.

Figure 2:
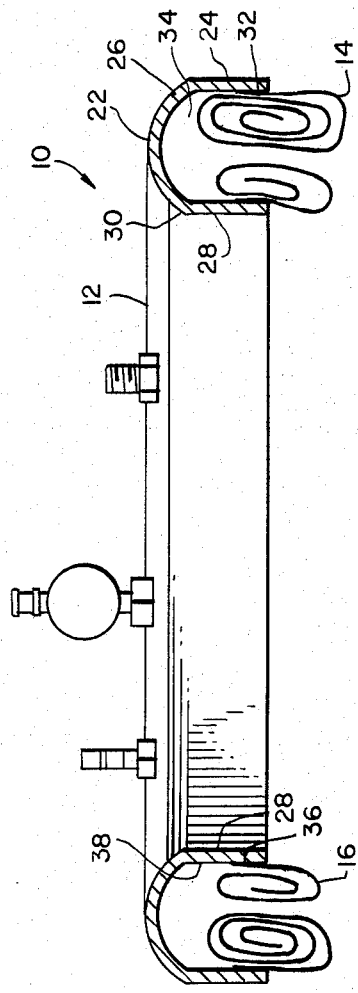

The flexible tubular chamber member 14 in non use condition is rolled up and partially fitted within the frame member 12. It should be noted that this upper end portion 32 of the chamber 14 is connected to the inner face 34 of the outer wall portion 24 by any suitable means, gluing for example, see FIG. 2. Similarly, the end portion 36 of elastic sealing sleeve 16 is suitably secured to the inner face 38 of the frame inner wall 28 in a rolled up manner as shown in FIG. 2.

For use in conncting the frame base 22 to the unit 20 said base is provided with a hose fitting 40, an exhaust valve 42 with hose fitting 44, and another hose fitting 46. The frame base 22 is also provided with a safety exhaust or relief valve 48. See FIG. 1.

The unit 20 for controlling flow of pressurized oxygen or other suitable gas to the chamber assembly 10 and exhausting same therefrom may be of the type described in Lasley U.S. Pat. No. 4,296,743 wherein a control device is disclosed which is completely fluid operated. For the purpose of making this disclosure clear a small portion of the description of such control device is set forth herein. Pressurized oxygen is fed through tube 60 to control box 62 and comes out of the said control box through tube 64 which introduces pressurized oxygen into chamber exhaust valve 42 to hold same in the closed condition as long as pressure is maintained therein. The main feed of pressurized oxygen comes out through the hose 66 into the chamber assembly 10 through connection 46. Tube 68 is connected to hose connection 40 and feeds pressurized gas from the chamber to a pressure gauge.

More specifically, the control box 62 includes a timer dial 70 with an on/off timer setting knob 72 and a cycle timing control screw 74. Chamber pressure gauge 76 measures the pressure in the chamber through tube 68. Pressure adjusting knob 78 controls operating pressure within the chamber. an air lite 80 is provided to determine when the device is operating. An air lite of this type is sold by C. A. Norgen, Company of Littleton, Colorado and is known as Rotowink Indicator.

In non-use condition the hyperbaric chamber is in the condition illustrated in FIG. 2 wherein the flexible tubular chamber member 14 is rolled up and partially fitted within the frame 12 and the sealing sleeve 16 is also rolled up and partially fitted with the frame 12.

In use, chamber assembly 10 in the condition illustrated in FIG. 2 is placed around the patient at either the chest, waist, upper arm or upper leg as required. The elastic sealing sleeve 16 is then rolled off the frame 12 down upon the patient's body so as to form an airtight seal therewith. Next the tubular chamber member 14 is unrolled downwardly past the patient's feet, see FIG. 3. Next the bottom 18 is folded over and secured in closed airtight condition by sealing tape 19. The airtight closure could also be formed bby rolling or even Zip Loc.

After this, the entire tubular chamber member 14 is sheathed in reinforcing means comprising a flexible large mesh net 21 made of plastic, wire or other suitable material. The sheath 21 is fastened together by any suitable means so as constrict and limit the expansion of the tubular chamber member 14 that might be brought about when the pressurized gas is introduced thereinto. The limiting of the expansion of the tubular chamber member 14 provides two advantages, namely less pressurized oxygen will be needed with a smaller volume, and less time will be required to fill the smaller volume.

With the hyperbaric chamber 10 assembled on the patient as set forth above, and illustrated in FIG. 4 of the drawings, the controls on control box 62 are operated to set the pressure cycles in operation whereby pressurized gas will be introduced into the chamber and then exhausted therefrom. Such action continues until the treatment time has expired.

The choice of materials for the various components of the hyperbaric chamber assembly 10 is quite varied. Plastics are generally used for most of the components. More specifically, the tubular chamber member 14 is made of clear plastic having sufficient rigidity that it will maintain its tubular configuration. It is, however, possible to use lighter weight plastic even though it might require slightly more care by the attendant and the patient. If necessary a framework may be provided to fit over the wound so that even a flexible tubular chamber member will not contact the wound. Latex combinations may be employed where resiliency is require.

The size of this unit may be varied so as to fit patients of various sizes. In addition various types of closure arrangement may be provided for the folded bottom 18 to assure an airtight seal for said bottom.

What is claimed is:

1. A portable and collapsible hyperbaric chamber assembly adapted to accommodate a major portion of a patient's body and adapted for connection to means for supplying pressurized oxygen or other suitable gas to and exhausting from said chamber, said chamber comprising a circular frame having a U-shaped cross section wherein the closed portion of the U constitutes the frame base and the depending portions form the inner and outer frame walls, said circular frame being sized to fit around the patient's torso, a flexible tubular chamber member having first and second open ends, said first open end being secured to the outer frame wall and extending downwardly therefrom, said tubular member having sufficient length whereby the second open end may be folded over and under the patient's feet, means for securing said open end in said folded position to seal the tubular chamber member from the ambient atmosphere, a sealing sleeve having first and second open ends, said sleeve extending within said tubular chamber member with said first open end thereof connected to the inner frame wall such that said second end extends downwardly therefrom, said sealing sleeve being sized to sealingly engage the upper portion of a patient's body, the frame base having mounting connection means adapted to receive pressurized oyygen or some other suitable gas, whereby a patient is positioned within the tubular chamber member and sealing sleeve with the sealing sleeve sealingly contacting the upper portion of the patient's body, then the tubular chamber member is folded below the patient's feet and secured by said securing means to form an airtight seal therein so that an airtight chamber is provided between the tubular chamber the patient's body and the sealing sleeve to receive the pressurized oxygen as required for treatment.

2. The invention as set forth in claim 1 and wherein the first open end of said flexible tubular chamber member is connected to the side of the outer frame wall adjacent the inner frame wall whereby the flexible tubular chamber member may be rolled up and positioned within the circular frame.

3. The invention as set forth in claim 1 and wherein the first open end of said sealing sleeve is connected to the side of the inner frame wall adjacent the outer frame wall whereby the sealing sleeve may be rolled up and positioned within the circular frame.

4. The invention as set forth in claim 1 and wherein the frame base is provided with an automatic pressure relief safety valve.

5. The invention as set forth in claim 1 and wherein the flexible tubular chamber member is provided with reinforcing means comprising a tubular sheath fastened to and encasing the flexible tubular chamber member so that there is no appreciable change in volume of the air tight chanber when under pressure operating conditions.

6. The invention as set forth in claim 1 and wherein said frame base is provided with an exhaust valve, a first connection adapted for connection with a pressurized oxygen source, and comprising said mounting connection means, a second connection adapted for connection with a pressure sensor and said exhaust valve is provided with a third connection means adapted for connection with a pressurized oxygen source for preventing the exhaust valve from opening as long as the pressurized oxygen is supplied thereto.

* * * * *